(12) United States Patent
Sung et al.

(10) Patent No.: US 10,253,411 B2
(45) Date of Patent: Apr. 9, 2019

(54) INORGANIC LAYER STRUCTURE INCLUDING ORGANIC LINKING MATERIAL, METHOD OF FABRICATING THE SAME, AND DISPLAY DEVICE INCLUDING THE SAME

(71) Applicant: IUCF-HYU (INDUSTRY-UNIVERSITY COOPERATION FOUNDATION HANYANG UNIVERSITY), Seoul (KR)

(72) Inventors: Myungmo Sung, Seoul (KR); Kyuseok Han, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 83 days.

(21) Appl. No.: 15/407,417

(22) Filed: Jan. 17, 2017

(65) Prior Publication Data

US 2017/0121812 A1    May 4, 2017

Related U.S. Application Data

(63) Continuation of application No. PCT/KR2015/007331, filed on Jul. 15, 2015.

(30) Foreign Application Priority Data

Jul. 15, 2014    (KR) .................. 10-2014-0088728

(51) Int. Cl.
*H01L 27/32*    (2006.01)
*C23C 16/40*    (2006.01)
(Continued)

(52) U.S. Cl.
CPC ............ *C23C 16/403* (2013.01); *C07F 5/068* (2013.01); *C23C 16/407* (2013.01);
(Continued)

(58) Field of Classification Search
None
See application file for complete search history.

(56) References Cited

U.S. PATENT DOCUMENTS 7,252,699 B2 *  8/2007  Perry ................. B22F 1/0018
                                                148/513
7,771,609 B2 *  8/2010  Leventis ........... C08G 18/3895
                                                252/62
(Continued)

FOREIGN PATENT DOCUMENTS

CN    102749753 A    10/2012
JP    2011-048374 A   3/2011
(Continued)

OTHER PUBLICATIONS

International Search Report of PCT/KR2015/007331 dated Sep. 10, 2015 [PCT/ISA/210].

*Primary Examiner* — Michael Lebentritt
(74) *Attorney, Agent, or Firm* — Sughrue Mion, PLLC (57) ABSTRACT

An inorganic layer structure is provided. The inorganic layer structure includes a metal oxide, and an organic linking material including a linking atom bonded to a metal atom of the metal oxide.

19 Claims, 7 Drawing Sheets

(51) Int. Cl.
*C07F 5/06* (2006.01)
*C23C 16/455* (2006.01)
*G02F 1/1333* (2006.01)
*H01L 51/00* (2006.01)
*H01L 51/52* (2006.01)
*C23C 28/00* (2006.01)
*C23C 28/04* (2006.01)
*G09F 9/33* (2006.01)
*G09F 9/35* (2006.01)

(52) U.S. Cl.
CPC .. *C23C 16/45529* (2013.01); *C23C 16/45553* (2013.01); *C23C 28/00* (2013.01); *C23C 28/04* (2013.01); *G02F 1/133305* (2013.01); *H01L 27/3244* (2013.01); *H01L 51/0081* (2013.01); *H01L 51/52* (2013.01); *G09F 9/33* (2013.01); *G09F 9/35* (2013.01); *H01L 51/0097* (2013.01); *H01L 51/5253* (2013.01)

(56) References Cited

U.S. PATENT DOCUMENTS

| | | | | |
|---|---|---|---|---|
| 8,841,471 B2* | 9/2014 | Yaghi | ............. | C07C 63/331 |
| | | | | 210/660 |
| 9,102,872 B2* | 8/2015 | Ueno | ............. | C09K 11/02 |
| 2002/0048639 A1* | 4/2002 | Negoro | ............. | C09K 19/3866 |
| | | | | 428/1.2 |
| 2005/0156176 A1* | 7/2005 | Gupta | ............. | H01L 51/0004 |
| | | | | 257/79 |
| 2008/0284320 A1* | 11/2008 | Karkkainen | ............. | B82Y 20/00 |
| | | | | 313/504 |
| 2009/0297799 A1* | 12/2009 | Nakasone | ............. | B41M 5/502 |
| | | | | 428/201 |
| 2011/0052836 A1* | 3/2011 | Kim | ............. | H01L 51/52 |
| | | | | 428/1.1 |
| 2012/0100417 A1* | 4/2012 | Ramprasad | ............. | H01M 10/052 |
| | | | | 429/163 |
| 2012/0119201 A1* | 5/2012 | Ueno | ............. | H01L 51/5048 |
| | | | | 257/40 |
| 2012/0238700 A1* | 9/2012 | Norwood | ............. | C08F 2/44 |
| | | | | 524/780 |
| 2013/0273461 A1* | 10/2013 | Liu | ............. | H01M 4/9008 |
| | | | | 429/535 |
| 2014/0166863 A1* | 6/2014 | Yamada | ............. | G01N 21/65 |
| | | | | 250/216 |

FOREIGN PATENT DOCUMENTS

| | | |
|---|---|---|
| KR | 10-2005-0107048 A | 11/2005 |
| KR | 10-2007-0109630 A | 11/2007 |
| WO | 2014/022330 A2 | 2/2014 |

\* cited by examiner

INORGANIC LAYER STRUCTURE INCLUDING ORGANIC LINKING MATERIAL, METHOD OF FABRICATING THE SAME, AND DISPLAY DEVICE INCLUDING THE SAME

CROSS-REFERENCE TO RELATED APPLICATION

This application is a continuation of pending International Application No. PCT/KR2015/007331, which was filed on Jul. 15, 2015 and claims priority to Korean Patent Application No. 10-2014-0088728, filed on Jul. 15, 2014, in the Korean Intellectual Property Office, the disclosures of which are hereby incorporated by reference in their entireties.

BACKGROUND

1. Field

Embodiments of the inventive concepts relate to an inorganic layer structure, a method of fabricating the same, and a display device including the same and, more particularly, to an inorganic layer structure including an organic linking material having linking atoms combined with metal atoms, a method of fabricating the same, and a display device including the same.

2. Description of the Related Art

A glass substrate used in display devices, picture frames, crafts, containers and the like has various advantages such as small coefficient of linear expansion, excellent gas barrier property, high optical transmittance, surface flatness, excellent heat resistance, and excellent chemical resistance. However, the glass substrate is weak to impact, is well broken, and is heavy by its high density.

As liquid crystal or organic light emitting display devices and electronic papers have been recently developed, techniques for replacing glass substrates of these display devices with plastic substrates have been studied. In other words, if the glass substrate is replaced with the plastic substrate, a total weight of the display device may be reduced and the flexibility of the design of the display device may be improved. In addition, the display device having the plastic substrate may be strong to impact. Furthermore, when the display device having the plastic substrate is fabricated by continuous processes, it may be more economical than the display device having the glass substrate.

Methods of performing various treatments on the plastic substrate are being studied to positively use these characteristics of the plastic substrate. For example, Korean Patent Registration No. 10-1296623 discloses a process of coating a plastic of polyethylenenaphthalate with an organic layer and a process of thermally treating the organic layer. Thus, a low-cost plastic substrate becomes planarized and uniform and the organic layer is hardened. In addition, it is possible to prevent interconnection lines of a display device from being abnormally formed by process heat generated in an array process. As a result, stability of fabricating processes of the display device may be improved.

SUMMARY

Embodiments of the inventive concepts may provide a highly reliable inorganic layer structure and a method of fabricating the same.

Embodiments of the inventive concepts may also provide an inorganic layer structure capable of minimizing generation of pin-holes and a method of fabricating the same.

Embodiments of the inventive concepts may further provide a flexible inorganic layer structure and a method of fabricating the same.

Embodiments of the inventive concepts may further provide an inorganic layer structure having a high resistance to moisture permeability and a method of fabricating the same.

Embodiments of the inventive concepts may further provide an inorganic layer structure having a high resistance to oxygen permeability and a method of fabricating the same.

Embodiments of the inventive concepts may further provide an electronic device including the inorganic layer structure according to some embodiments of the inventive concepts or the inorganic layer structure fabricated by the fabricating method according to some embodiments of the inventive concepts.

In an aspect, an inorganic layer structure may include a metal oxide, and an organic linking material including a linking atom bonded to a metal atom of the metal oxide.

In some embodiments, the organic linking material may be connected to the metal atom of the metal oxide disposed under the organic linking material and the metal atom of the metal oxide disposed on the organic linking material.

In some embodiments, the organic linking material may include a first organic linker and a second organic linker adjacent to each other, and a linking atom of the first organic linker may be bonded to a linking atom of the second organic linker.

In some embodiments, each of the linking atom of the first organic linker and the linking atom of the second organic linker may be bonded to a plurality of the metal atoms included in the metal oxide.

In some embodiments, the number of the metal atoms bonded to the linking atom of the first organic linker may be equal to the number of the metal atoms bonded to the linking atom of the second organic linker.

In some embodiments, bonds between the linking atom and the plurality of metal atoms may be coordinate covalent bonds.

In some embodiments, a content of the organic linking material may be less than a content of the metal oxide.

In some embodiments, the organic linking material may include a first linking atom and a second linking atom, and at least one of the first linking atom or the second linking atom may include a chalcogen atom.

In some embodiments, the number of the metal atom of the metal oxide bonded to the first linking atom may be different from the number of the metal atom of the metal oxide bonded to the second linking atom.

In some embodiments, a kind of a bond between the first linking atom and the metal atom may be different from a kind of a bond between the second linking atom and the metal atom.

In some embodiments, the organic linking material may include a plurality of organic linkers. The plurality of organic linkers disposed at the same level may be defined as a group, and the organic linking material may include a plurality of the groups spaced apart from each other.

In some embodiments, the organic linking material may include an organic linker, and the organic linker may include an organic compound, a first linking atom bonded to the organic compound, and a second linking atom bonded to the organic compound.

In some embodiments, the first linking atom and the second linking atom may be located at para positions with respect to the organic compound.

In some embodiments, the first linking atom may be bonded to the metal atom included in the metal oxide disposed under the organic linker, and the second linking atom may be bonded to the metal atom included in the metal oxide disposed on the organic linker. The number of the metal atom bonded to the second linking atom may be more than the number of the metal atom bonded to the first linking atom.

In an aspect, embodiments of the inventive concepts may provide a display device.

In some embodiments, the display device may include the inorganic layer structure according to embodiments of the inventive concepts, a selection device layer on the inorganic layer structure, and an optical device layer on the selection device layer.

In some embodiments, the display device may include a selection device layer on a substrate, an optical device layer on the selection device layer, and the inorganic layer structure of the embodiment of the inventive concepts disposed on the optical device layer.

In an aspect, a method of fabricating an inorganic layer structure may include preparing a substrate, providing a first source including a metal and a second source including oxygen onto the substrate to form a first metal oxide, providing the first source and a third source including an organic linker having first and second linking atoms onto the first metal oxide to form an organic linking material having the first linking atom bonded to a metal atom of the first source provided on the first metal oxide, and providing the first source and the second source onto the organic linking material to form a second metal oxide having a metal atom bonded to the second linking atom of the organic linker.

In some embodiments, the providing of the first source and the second source onto the substrate to form the first metal oxide may be repeatedly performed a plurality of times, and the providing of the first source and the second source onto the organic linking material to form the second metal oxide may be repeatedly performed a plurality of times.

In some embodiments, the number of times to repeat the providing of the first source and the second source onto the substrate to form the first metal oxide may be equal to the number of times to repeat the providing of the first source and the second source onto the organic linking material to form the second metal oxide.

In some embodiments, the number of times to repeat the providing of the first source and the third source to form the organic linking material may be less than the number of times to repeat the providing of the first source and the second source to form the first metal oxide and the number of times to repeat the providing of the first source and the second source to form the second metal oxide.

DETAILED DESCRIPTION OF THE EMBODIMENTS

The inventive concepts will now be described more fully hereinafter with reference to the accompanying drawings, in which exemplary embodiments of the inventive concepts are shown. It should be noted, however, that the inventive concepts are not limited to the following exemplary embodiments, and may be implemented in various forms. Accordingly, the exemplary embodiments are provided only to disclose the inventive concepts and let those skilled in the art know the category of the inventive concepts.

It will be understood that when an element such as a layer, region or substrate is referred to as being "on" another element, it can be directly on the other element or intervening elements may be present. In addition, in the drawings, the thicknesses of layers and regions are exaggerated for clarity.

It will be also understood that although the terms first, second, third etc. may be used herein to describe various elements, these elements should not be limited by these terms. These terms are only used to distinguish one element from another element. Thus, a first element in some embodiments could be termed a second element in other embodiments without departing from the teachings of the present invention. Exemplary embodiments of aspects of the present inventive concepts explained and illustrated herein include their complementary counterparts. As used herein, the term "and/or" includes any and all combinations of one or more of the associated listed items.

The terminology used herein is for the purpose of describing particular embodiments only and is not intended to limit the invention. As used herein, the singular terms "a", "an" and "the" are intended to include the plural forms as well, unless the context clearly indicates otherwise. It will be further understood that the terms "comprises", "comprising", "includes", "including", "have", "has" and/or "having" when used herein, specify the presence of stated features, integers, steps, operations, elements, and/or components, but do not preclude the presence or addition of one or more other features, integers, steps, operations, elements, components, and/or groups thereof. Furthermore, it will be understood that when an element is referred to as being "connected" or "coupled" to another element, it may be directly connected or coupled to the other element or intervening elements may be present.

In addition, in explanation of the present invention, the descriptions to the elements and functions of related arts may be omitted if they obscure the subjects of the inventive concepts.

Figure 1:
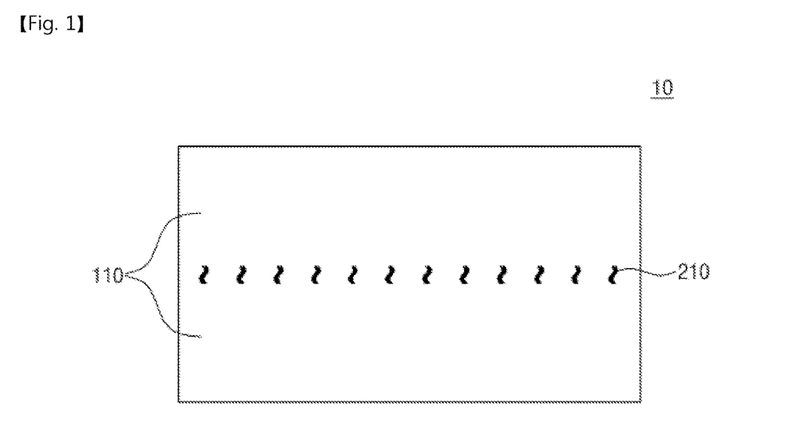
FIG. 1 is a view illustrating an inorganic layer structure according to some embodiments of the inventive concepts.

FIG. 1 is a view illustrating an inorganic layer structure according to some embodiments of the inventive concepts.

Referring to FIG. 1, an inorganic layer structure 10 according to some embodiments of the inventive concepts may include a metal oxide 110 and an organic linking material 210.

The metal oxide 110 may include metal atoms. For example, the metal oxide 110 may include at least one of zinc (Zn), tin (Sn), indium (In), cadmium (Cd), aluminum (Al), titanium (Ti), manganese (Mn), iron (Fe), cobalt (Co), copper (Cu), or tungsten (W).

In some embodiments, an entire portion of the metal oxide 110 may be formed of the same material. For example, the metal oxide 110 may be formed of aluminum oxide ($Al_2O_3$). Alternatively, in other embodiments, the metal oxide 110 may be formed of a plurality of materials different from each other.

In some embodiments, the lowermost portion of the inorganic layer structure 10 may be a portion of the metal oxide 110, and the uppermost portion of the inorganic layer structure 10 may be a portion of the metal oxide 110.

In some embodiments, in the inorganic layer structure 10, an occupying weight or thickness of the metal oxide 110 may be higher than an occupying weight or thickness of the organic linking material 210.

The organic linking material 210 may be combined with the metal atoms of the metal oxide 110. In some embodiments, the organic linking material 210 may be connected to the metal atoms of the portion of the metal oxide 110 disposed under the organic linking material 210 and the metal atoms of the portion of the metal oxide 110 disposed on the organic linking material 210.

The organic linking material 210 may include a plurality of organic linkers. A plurality of the organic linkers disposed at the same level may be defined as one group. Here, the term 'level' means a height of the organic linker from a substrate on which the inorganic layer structure 10 is disposed and/or formed. The inorganic layer structure 10 according to some embodiments of the inventive concepts may include a plurality of the groups spaced apart from each other.

In some embodiments, the organic linking material 210 may include an organic compound. When the organic linking material 210 is provided in plurality, the plurality of organic linking materials 210 may include the same organic compound. For example, the organic compound may be an aromatic compound.

The organic linking material 210 may include linking atoms. The linking atoms may be bonded to or combined with the metal atoms included in the metal oxide 110. For example, as illustrated in FIG. 1, the linking atoms of the organic linking material 210 may be bonded and connected to the metal atoms of a portion of the metal oxide 110 adjacent to a bottom end portion of the organic linking material 210 and the metal atoms of a portion of the metal oxide 110 adjacent to a top end portion of the organic linking material 210.

The organic linkers included in the organic linking material 210 will be described in more detail with reference to FIG. 2.

Figure 2:
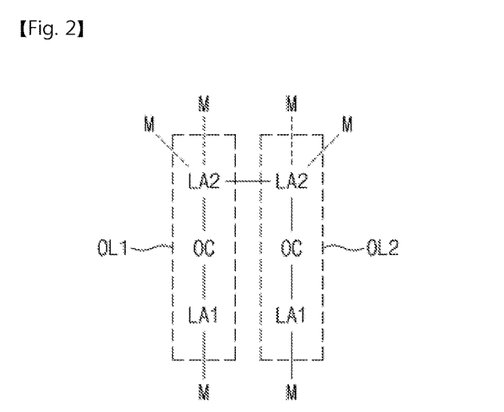
FIG. 2 is a view illustrating an embodiment of an organic linker contained in an organic linking material included in an inorganic layer structure according to some embodiments of the inventive concepts.

FIG. 2 is a view illustrating an embodiment of an organic linker contained in an organic linking material included in an inorganic layer structure according to some embodiments of the inventive concepts.

Referring to FIG. 2, the organic linking material according to some embodiments of the inventive concepts may include a first organic linker OL1 and a second organic linker OL2. Each of the first and second organic linkers OL1 and OL2 may include an organic compound OC, a first linking atom LA1 combined with the organic compound OC, and a second linking atom LA2 combined with the organic compound OC.

At least one of the first linking atom LA1 or the second linking atom LA2 may include a chalcogen atom. For example, when one of the first and second linking atoms LA1 and LA2 includes sulfur (S), the other of the first and second linking atoms LA1 and LA2 may include at least one of O, S, N, NH, or CO.

In some embodiments, the first linking atom LA1 may be oxygen (O), the second linking atom LA2 may be sulfur (S), and the metal atom M may be aluminum (Al).

The first linking atom LA1 and the second linking atom LA2 may be located at para positions with respect to the organic compounds OC, as illustrated in FIG. 2. Unlike FIG. 2, the first linking atom LA1 and the second linking atom LA2 may be located at ortho positions or meta positions with respect to the organic compounds OC.

The first and second linking atoms LA1 and LA2 may be bonded to or combined with the metal atoms M of the metal oxide 110 described with reference to FIG. 1. For example, the first linking atoms LA1 may be bonded to the metal atoms M of the metal oxide disposed under the organic linkers OL1 and OL2. In this case, the metal oxide disposed under the organic linkers OL1 and OL2 may mean a metal oxide that is previously formed before the organic linkers OL1 and OL2 are deposited. The second linking atoms LA2 may be bonded to the metal atoms M of the metal oxide disposed on the organic linkers OL1 and OL2. In this case, the metal oxide disposed on the organic linkers OL1 and OL2 may mean a metal oxide that is formed on the organic linkers OL1 and OL2 after the organic linkers OL1 and OL2 are deposited.

The first linking atoms LA1 may be bonded to each other or the second linking atoms LA2 may be bonded to each other. For example, as illustrated in FIG. 2, the second linking atom LA2 of the first organic linker OL1 and the second linking atom LA2 of the second organic linker OL2 may be adjacent to each other and may be bonded to each other. In some embodiments, in this case, the second linking atom LA2 may be sulfur (S). Unlike the second linking atoms LA2, the first linking atom LA1 of the first organic linker OL1 and the first linking atom LA1 of the second organic linker OL2 may be adjacent to each other but may not be bonded to each other. In some embodiments, in this case, the first linking atom LA1 may be oxygen (O).

When the second linking atoms LA2 of the first and second organic linkers OL1 and OL2 are bonded to each other, each of the second linking atoms LA2 may be bonded to a plurality of the metal atoms M included in the metal oxide. In some embodiments, the number of the metal atoms M bonded to the second linking atom LA2 of the first organic linker OL1 may be equal to the number of the metal atoms M bonded to the second linking atom LA2 of the second organic linker OL2. In some embodiments, in this case, each of the second linking atoms LA2 may be bonded to the plurality of metal atoms M to form coordinate covalent bonds.

Unlike the second linking atoms LA2, each of the first linking atoms LA1 not bonded to each other may be bonded to the metal atom M of the metal oxide in one-to-one correspondence. In some embodiments, in this case, each of the first linking atoms LA1 may be bonded to the metal atom M to form a covalent bond.

Thus, the number of the metal atom M bonded to the first linking atom LA1 may be less than the number of the metal atoms M bonded to the second linking atom LA2. In addition, a kind of the bond between the first linking atom LA1 and the metal atom M may be different from a kind of the bond between the second linking atom LA2 and the metal atom M.

The inorganic layer structure according to some embodiments of the inventive concepts may include the organic linking material having the linking atom bonded to the metal atom included in the metal oxide, and the linking atom may be bonded to a plurality of the metal atoms included in the metal oxide. Thus, it is possible to provide the highly reliable inorganic layer structure having a high resistance to moisture permeability and a high resistance to oxygen permeability in a flexible state.

FIG. 1 illustrates one group consisting of the organic linkers located at the same level. However, embodiments of the inventive concepts are not limited thereto. In certain embodiments, the group may be provided in plurality in the metal oxide or the organic linkers may be randomly dispersed in the metal oxide. These will be described with reference to FIGS. 3 and 4.

Figure 3:
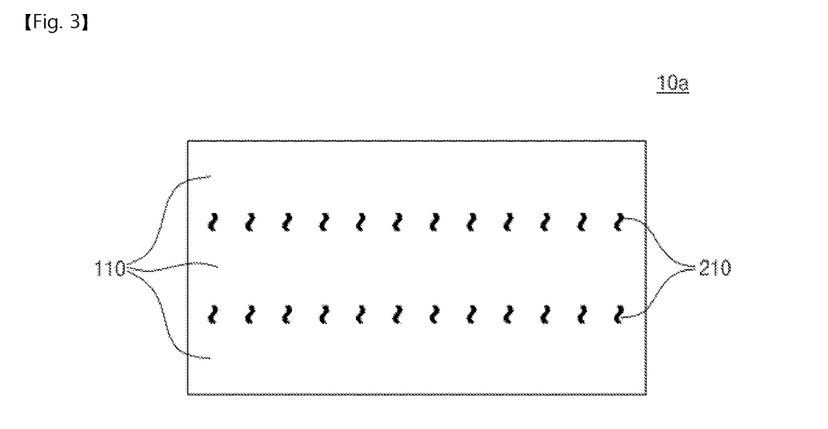
FIG. 3 is a view illustrating an inorganic layer structure according to other embodiments of the inventive concepts.

FIG. 3 is a view illustrating an inorganic layer structure according to other embodiments of the inventive concepts.

Referring to FIG. 3, an organic linking material 210 of an inorganic layer structure 10a according to other embodiments of the inventive concepts may include a plurality of groups of which each includes a plurality of organic linkers disposed at the same level, unlike the inorganic layer structure 10 described with reference to FIG. 1.

The plurality of groups may be disposed at levels different from each other and may be spaced apart from each other. In this case, the organic linkers included in one group may be formed simultaneously with each other by the same process but may not be formed simultaneously with the organic linkers included in other group.

In FIG. 3, two groups are provided in the inorganic layer structure 10a. However, embodiments of the inventive concepts are not limited thereto. In certain embodiments, three or more groups may be provided in the inorganic layer structure 10a. In some embodiments, in this case, portions of the metal oxide 110, each of which is disposed between the groups adjacent to each other, may have thicknesses substantially equal to each other. Alternatively, portions of the metal oxide 110, each of which is disposed between the groups adjacent to each other, may have thicknesses different from each other. For example, the thickness of the portion of the metal oxide located relatively high may be greater or less than the thickness of the portion of the metal oxide located relatively low.

Figure 4:
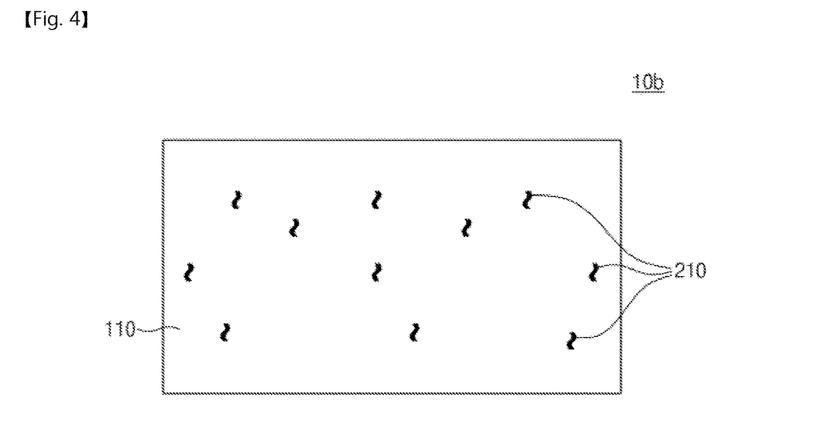
FIG. 4 is a view illustrating an inorganic layer structure according to still other embodiments of the inventive concepts.

FIG. 4 is a view illustrating an inorganic layer structure according to still other embodiments of the inventive concepts.

Referring to FIG. 4, an organic linking material 210 of an inorganic layer structure 10b according to still other embodiments of the inventive concepts may include organic linkers randomly dispersed in the metal oxide 110, unlike the inorganic layer structure 10 described with reference to FIG. 1.

A method of fabricating an inorganic layer structure according to some embodiments of the inventive concepts will be described hereinafter with reference to FIG. 5.

Figure 5:
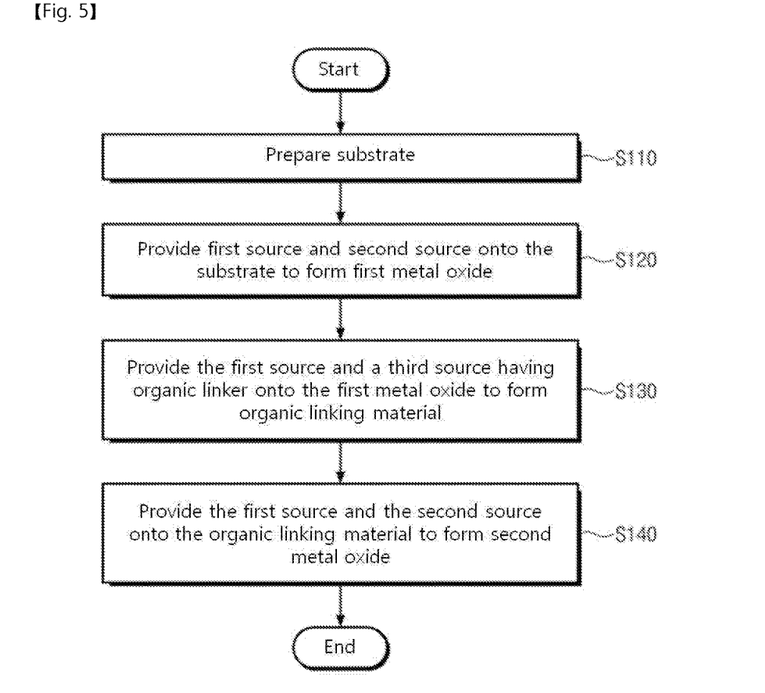
FIG. 5 is a flow chart illustrating a method of fabricating an inorganic layer structure, according to some embodiments of the inventive concepts.

FIG. 5 is a flow chart illustrating a method of fabricating an inorganic layer structure, according to some embodiments of the inventive concepts.

Referring to FIG. 5, a substrate is prepared (S110). In some embodiments, the substrate may be prepared in a chamber for performing an atomic layer deposition process and a molecular layer deposition process. The substrate may be a flexible substrate. For example, the substrate may be a plastic substrate. Alternatively, the substrate may be a semiconductor substrate or a glass substrate. In still other embodiments, the substrate may be a substrate including at least one of a transistor, a memory, a diode, a solar cell, an optical device, a bio-sensor, a nano-electro-mechanical system (NEMS), a micro-electro-mechanical system MEMS), a nano-device, or a chemical sensor.

A first source and a second source may be provided onto the substrate to form a first metal oxide (S120). The first source may include metal atoms, and the second source may include oxygen. To form the first metal oxide, the process of providing the first source and the second source onto the substrate may be repeatedly performed a plurality of times. For example, the first metal oxide may be formed by repeatedly performing a process cycle including a process of providing the first source, a process of providing a purge gas, a process of providing the second source, and a process of providing a purge gas.

In some embodiments, the first metal oxide may be formed by the atomic layer deposition (ALD) process. For example, when the first source includes aluminum, the first source may be trimethylaluminum. In this case, the first metal oxide may be aluminum oxide (e.g., $Al_2O_3$). For another example, when the first source includes zinc, the first source may be diethylzinc. In this case, the first metal oxide may be zinc oxide (e.g., ZnO). Alternatively, the first metal oxide may be formed by at least one of other various processes such as a chemical vapor deposition (CVD) process, a physical vapor deposition (PVD) process, and an electron-beam evaporation process.

After the first metal oxide is formed, the first source and a third source may be provided onto the first metal oxide to form an organic linking material (S130). The third source may include an organic linker having first and second linking atoms, as described with reference to FIG. 2.

The first source may be provided onto the first metal oxide, and then, the third source may be provided to form the organic linking material. Thus, the metal atom included in the first source provided on the first metal oxide may be bonded to the first linking atom of the organic linker of the third source. In some embodiments, to form the organic linking material, the process of providing the first source and the third source may be performed one time.

In some embodiments, the third source may include the organic linker including sulfur (S). For example, the third source may include at least one of 4-mercaptophenol, 2-sulfanylphenol, 3-Sulfanylphenol, benzenedithiol, 1,3-Benzenedithiol, or 1,4-Benzenedithiol.

The first linking atom of the organic linking material may be bonded to the metal atom of the first source provided on the first metal oxide prior to the third source as described above. For example, when the third source is 4-mercaptophenol and the first source is trimethylaluminum, the first linking atom of the organic linking material may be oxygen (O) and may be bonded to the aluminum (Al).

After the formation of the organic linking material, the first source and the second source may be provided onto the organic linking material to form a second metal oxide (S140). The second metal oxide may be formed by repeatedly performing a process cycle including a process of providing the first source, a process of providing a purge gas, a process of providing the second source, and a process of providing a purge gas.

The metal atom included in the first source provided on the organic linking material may be bonded to the second linking atom of the organic linking material. In other words, the metal atom of the lowermost portion of the second metal oxide may be bonded to the second linking atom. In this case, the second linking atom may be bonded to a plurality of the metal atoms of the lowermost portion of the second metal oxide, and the bonds between the second linking atom and the plurality of metal atoms may be the coordinate covalent bonds, as described with reference to FIG. 2. The metal atoms of a residual portion located on the lowermost portion of the second metal oxide may not be bonded to the second linking atom of the organic linking material.

In some embodiments, the number of times to repeat the process of providing the first source and the second source for the formation of the second metal oxide may be equal to the number of times to repeat the process of providing the first source and the second source for the formation of the first metal oxide. Alternatively, in other embodiments, the number of times to repeat the process of providing the first source and the second source for the formation of the second metal oxide may be different from the number of times to repeat the process of providing the first source and the second source for the formation of the first metal oxide.

In some embodiments, the process of forming the second metal oxide may be the substantially same as the process (e.g., the ALD process) of forming the first metal oxide. Alternatively, in other embodiments, the second metal oxide may be formed by a process different from the process of forming the first metal oxide.

The process of providing the first and third sources for the formation of the organic linking material described with reference to FIG. 5 may further be provided on the second metal oxide after the formation of the second metal oxide. In other words, the process of providing the first and second sources to form the metal oxide and the process of providing the first and third sources to form the organic linking material may be defined as a unit process, and the unit process may be repeatedly performed a plurality of times to fabricate the inorganic layer structure according to some embodiments of the inventive concepts.

Embodiments of a display device including the inorganic layer structure according to embodiments of the inventive concepts or the inorganic layer structure fabricated according to the fabricating method will be described hereinafter with reference to FIGS. 6 and 7.

Figure 6:
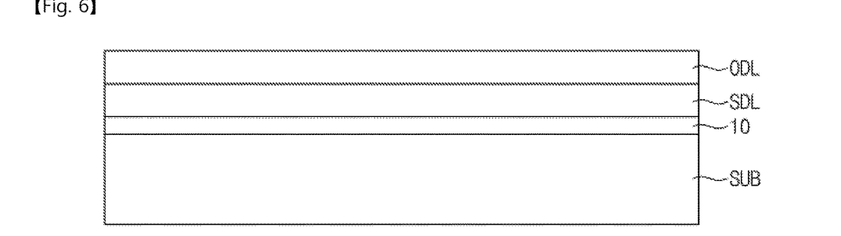
FIG. 6 is a view illustrating an embodiment of a display device including an inorganic layer structure according to some embodiments of the inventive concepts.

FIG. 6 is a view illustrating an embodiment of a display device including an inorganic layer structure according to some embodiments of the inventive concepts.

Referring to FIG. 6, the inorganic layer structure 10 according to embodiments of the inventive concepts is provided on a substrate SUB. The inorganic layer structure 10 may be one of the inorganic layer structures described with reference to FIGS. 1 to 4 or the inorganic layer structure fabricated according to the fabricating method described with reference to FIG. 5.

A selection device layer SDL may be disposed on the inorganic layer structure 10. The inorganic layer structure 10 may be disposed between the selection device layer SDL and the substrate SUB. The selection device layer SDL may include devices for selecting pixel cells included in a display device. For example, the selection device layer SDL may include at least one of a thin film transistor or a diode.

An optical device layer ODL may be disposed on the selection device layer SDL. The optical device layer ODL may include devices emitting light in the pixel cells of the display device. For example, the optical device layer ODL may include at least one of an organic light emitting diode or a liquid crystal layer.

Unlike FIG. 6, the inorganic layer structure 10 may be disposed on the optical device layer ODL. This will be described with reference to FIG. 7.

Figure 7:
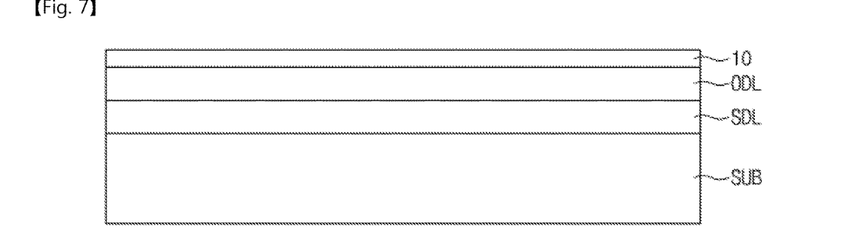
FIG. 7 is a view illustrating another embodiment of a display device including an inorganic layer structure according to some embodiments of the inventive concepts.

FIG. 7 is a view illustrating another embodiment of a display device including an inorganic layer structure according to some embodiments of the inventive concepts.

Referring to FIG. 7, the substrate SUB of FIG. 6 may be provided, and the selection device layer SDL of FIG. 6 may be provided on the substrate SUB. The optical device layer ODL of FIG. 6 may be provided on the selection device layer SDL. The inorganic layer structure 10 may be disposed on the optical device layer ODL. In other words, the selection device layer SDL and the optical device layer ODL may be disposed between the inorganic layer structure 10 and the substrate SUB.

According to still other embodiments of the inventive concepts, one inorganic layer structure 10 may be provided between the substrate SUB and the selection device layer SDL and another inorganic layer structure 10 may be provided on the optical device layer ODL, unlike FIGS. 6 and 7.

The display device according to some embodiments of the inventive concepts may include the inorganic layer structure which is flexible and has the high resistance to moisture permeability and the high resistance to oxygen permeability. Thus, it is possible to provide the flexible display device having long lifetime and high reliability.

In the embodiments of FIGS. 6 and 7, the display devices include the inorganic layer structures according to embodiments of the inventive concepts. However, embodiments of the inventive concepts are not limited thereto. In certain embodiments, the inorganic layer structures according to embodiments of the inventive concepts may be applied to other various electronic devices.

Test results of characteristics of the inorganic layer structures according to embodiments of the inventive concepts will be described hereinafter.

Figure 8:
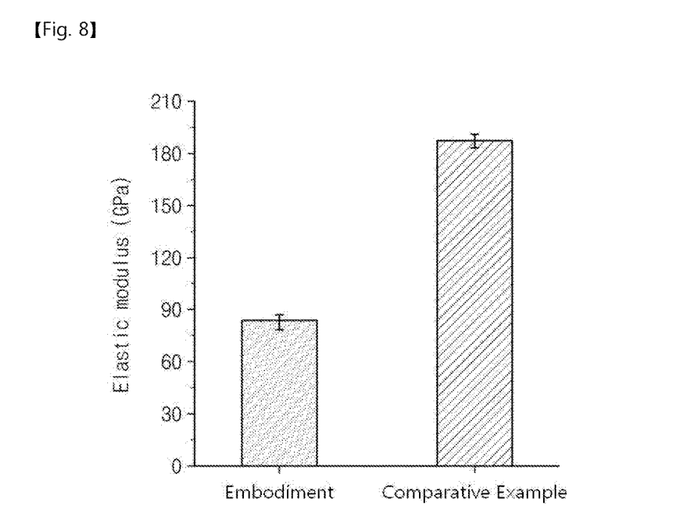
FIG. 8 is a graph illustrating an elastic modulus of an inorganic layer structure according to some embodiments of the inventive concepts.
Figure 9:
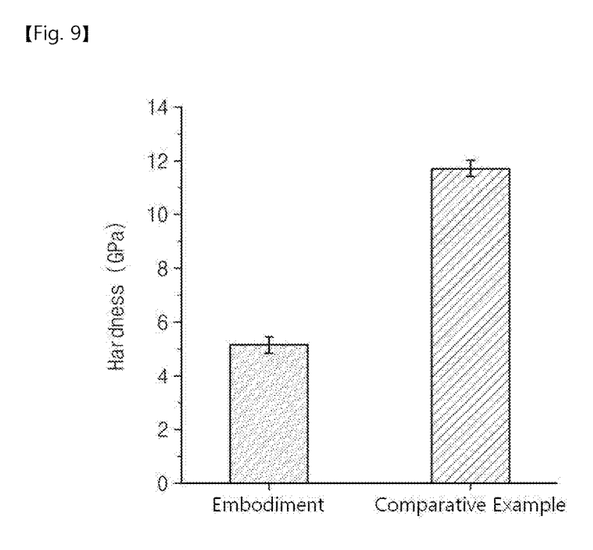
FIG. 9 is a graph illustrating a hardness of an inorganic layer structure according to some embodiments of the inventive concepts.

FIG. 8 is a graph illustrating an elastic modulus of an inorganic layer structure according to some embodiments of the inventive concepts, and FIG. 9 is a graph illustrating a hardness of an inorganic layer structure according to some embodiments of the inventive concepts.

Referring to FIGS. 8 and 9, to test characteristics of the inorganic layer structure according to embodiments of the inventive concepts, the inorganic layer structure according to an embodiment of the inventive concepts was fabricated by repeatedly performing a first process of depositing $Al_2O_3$ by using trimethylaluminum and $H_2O$ as the first source and the second source and a second process of depositing an organic linking material on $Al_2O_3$ by using trimethylaluminum and 4-mercaptophenol as the first source and the third source a plurality of times.

The second process of depositing the organic linking material was omitted and the first process of depositing $Al_2O_3$ was performed to form an inorganic layer structure uses as a comparative example to the inorganic layer structure according to the embodiments of the inventive concepts.

An elastic modulus and a hardness of the inorganic layer structure fabricated according to the aforementioned embodiment of the inventive concepts were measured, and an elastic modulus and a hardness of the inorganic layer structure fabricated according to the comparative example were measured. As shown in FIGS. 8 and 9, the elastic modulus and the hardness of the inorganic layer structure according to the embodiment of the inventive concepts are lower than the elastic modulus and the hardness of the inorganic layer structure according to the comparative example. In other words, the flexible characteristic of the inorganic layer structure including the organic linking material according to the embodiment of the inventive concepts is better than that of the inorganic layer structure not including the organic linking material.

Figure 10:
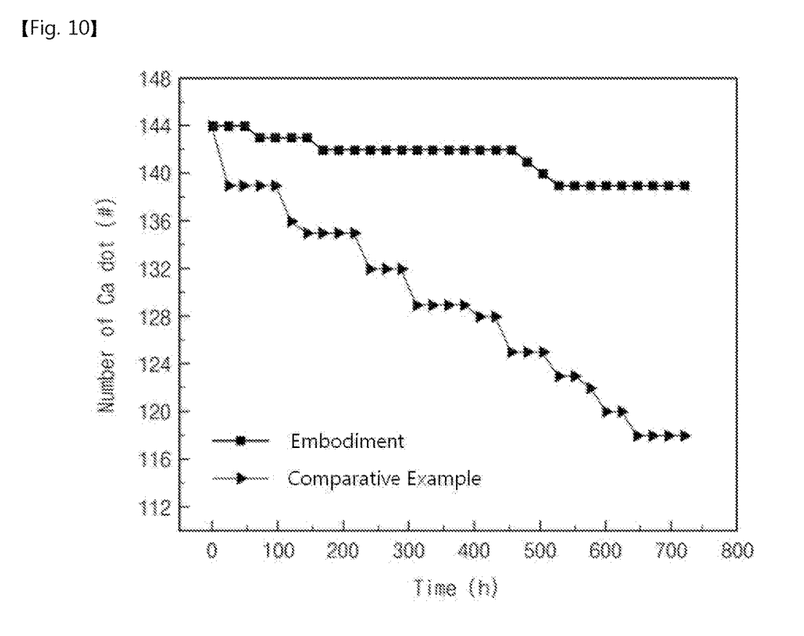
FIG. 10 is a graph illustrating a resistance to moisture permeability of an inorganic layer structure according to some embodiments of the inventive concepts.

FIG. 10 is a graph illustrating a resistance to moisture permeability of an inorganic layer structure according to some embodiments of the inventive concepts.

Referring to FIG. 10, an inorganic layer structure according to an embodiment of the inventive concepts, in which 144 calcium (Ca) dots were inserted, was fabricated using trimethylaluminum and 4-mercaptophenol as described with reference to FIGS. 8 and 9. An inorganic layer structure according to a comparative example, in which 144 Ca dots were inserted, was fabricated using trimethylaluminum. The organic linking material was omitted from the inorganic layer structure according to the comparative example. Variations over time of the Ca dots included in the inorganic layer structures according to the embodiment and the comparative example were observed under conditions of a temperature of 70 degrees Celsius and a humidity of 70%, and the observed results were illustrated in FIG. 10.

The Ca dots included in the inorganic layer structure according to the comparative example were rapidly reduced as time passed. However, a reduction of the Ca dots included in the inorganic layer structure according to the embodiment of the inventive concepts was significantly less than a reduction of the Ca dots included in the inorganic layer structure according to the comparative example.

The following table 1 shows WVTR of the inorganic layer structures according to the embodiment and the comparative example. As shown in the following table 1 and FIG. 10, the inorganic layer structure including the organic linking material according to the embodiment of the inventive concepts has excellent resistance to moisture permeability/resistance to oxygen permeability, as compared with the inorganic layer structure according to the comparative example. In other words, the method of providing the organic linking material into an inorganic layer may effectively improve the resistance to moisture permeability/the resistance to oxygen permeability of the inorganic layer.

TABLE 1

| | WVTR (g/m² day) |
|---|---|
| Embodiment | $5.1 \times 10^{-7}$ |
| Comparative Example | $1.2 \times 10^{-6}$ |

Figure 11:
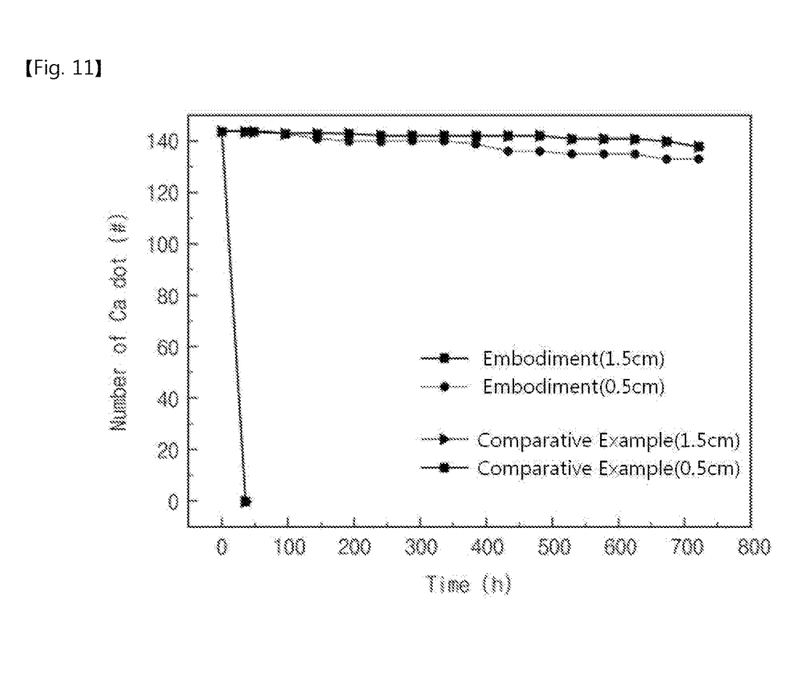
FIG. 11 is a graph illustrating a flexible characteristic of an inorganic layer structure according to some embodiments of the inventive concepts.

FIG. 11 is a graph illustrating a flexible characteristic of an inorganic layer structure according to some embodiments of the inventive concepts.

Referring to FIG. 11, an inorganic layer structure according to an embodiment of the inventive concepts, in which 144 Ca dots were inserted, was fabricated using trimethylaluminum and 4-mercaptophenol as described with reference to FIGS. 8 and 9. An inorganic layer structure according to a comparative example, in which 144 Ca dots were inserted, was fabricated using trimethylaluminum. The organic linking material was omitted from the inorganic layer structure according to the comparative example. Variations over time of the Ca dots included in the inorganic layer structures according to the embodiment and the comparative example were observed under conditions of bending radii of 0.5 cm and 1.5 cm, a temperature of 70 degrees Celsius, and a humidity of 70%, and the observed results were illustrated in FIG. 11.

The Ca dots included in the inorganic layer structure according to the comparative example were rapidly reduced as time passed. However, a reduction of the Ca dots included in the inorganic layer structure according to the embodiment of the inventive concepts was significantly less than a reduction of the Ca dots included in the inorganic layer structure according to the comparative example.

The following table 2 shows WVTR of the inorganic layer structures according to the embodiment and the comparative example. As shown in the following table 2 and FIG. 11, the inorganic layer structure including the organic linking material according to the embodiment of the inventive concepts also has excellent resistance to moisture permeability/resistance to oxygen permeability in a bending state, as compared with the inorganic layer structure according to the comparative example. In other words, the method of providing the organic linking material into the inorganic layer may effectively improve the resistance to moisture permeability/the resistance to oxygen permeability of the inorganic layer in a flexible state.

TABLE 2

| | Bending radius(cm) | WVTR (g/m² day) |
|---|---|---|
| Embodiment | 1.5 | $9.1 \times 10^{-7}$ |
| | 0.5 | $2.3 \times 10^{-6}$ |
| Comparative Example | 1.5 | $>\sim 10^{-1}$ |
| | 0.5 | $>\sim 10^{-1}$ |

The inorganic layer structure and the method of fabricating the same according to embodiments of the inventive concepts may be used to improve reliability of various electronic devices such as a display device and a memory device.

The inorganic layer structure according to embodiments of the inventive concepts includes the metal oxide, and the organic linking material having the linking atom bonded to the metal atom of the metal oxide. Thus, it is possible to provide the flexible inorganic layer structure having the high resistance to moisture permeability, the high resistance to oxygen permeability, and the high reliability.

In addition, the display device according to embodiments of the inventive concepts may include the inorganic layer structure having the organic linking material. Thus, it is possible to provide the display device having the long lifetime and the high reliability.

While the inventive concepts have been described with reference to exemplary embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. An inorganic layer structure comprising:
a metal oxide; and
an organic linking material including a linking atom bonded to a metal atom of the metal oxide,
wherein the organic linking material includes, a first linking atom and a second linking atom, and
wherein at least one of the first linking atom or the second linking atom includes a chalcogen atom.

2. The inorganic layer structure of claim 1, wherein the organic linking material is connected to the metal atom of the metal oxide disposed under the organic linking material and the metal atom of the metal oxide disposed on the organic linking material.

3. The inorganic layer structure of claim 1, wherein the organic linking material includes a first organic linker and a second organic linker which are adjacent to each other, and
wherein a linking atom of the first organic linker is bonded to a linking atom of the second organic linker.

4. The inorganic layer structure of claim 3, wherein each of the linking atom of the first organic linker and the linking atom of the second organic linker is bonded to a plurality of the metal atoms included in the metal oxide.

5. The inorganic layer structure of claim 4, wherein the number of the metal atoms bonded to the linking atom of the first organic linker is equal to the number of the metal atoms bonded to the linking atom of the second organic linker.

6. An inorganic layer structure comprising:
a metal oxide; and
an organic linking material including a linking atom bonded to a metal atom of the metal oxide,
wherein the organic linking material includes a first organic linker and a second organic linker which are adjacent to each other,
wherein a linking atom of the first organic linker is bonded to a linking atom of the second organic linker,
wherein each of the linking atom of the first organic linker and the linking atom of the second organic linker is bonded to a plurality of the metal atoms included in the metal oxide, and
wherein bonds between the linking atom and the plurality of metal atoms are coordinate covalent bonds.

7. The inorganic layer structure of claim 1, wherein an amount of the organic linking material is less than an amount of the metal oxide.

8. The inorganic layer structure of claim 1, wherein a number of the metal atom of the metal oxide bonded to the first linking atom is different from a number of the metal atom of the metal oxide bonded to the second linking atom.

9. The inorganic layer structure of claim 1, wherein a type of chemical bond between the first linking atom and the metal atom is different from a type of chemical bond between the second linking atom and the metal atom.

10. The inorganic layer structure of claim 1, wherein the organic linking material includes a plurality of organic linkers,
wherein the plurality of organic linkers disposed at the same level is defined as a group, and
wherein the organic linking material includes a plurality of the groups spaced apart from each other.

11. The inorganic layer structure of claim 1, wherein the organic linking material includes an organic linker, and
wherein the organic linker includes: an organic compound; a first linking atom bonded to the organic compound; and a second linking atom bonded to the organic compound.

12. The inorganic layer structure of claim 11, wherein the first linking atom and the second linking atom are located at para positions with respect to the organic compound.

13. The inorganic layer structure of claim 11, wherein the first linking atom is bonded to the metal atom included in the metal oxide disposed under the organic linker,
wherein the second linking atom is bonded to the metal atom included in the metal oxide disposed on the organic linker, and
wherein the number of the metal atom bonded to the second linking atom is more than the number of the metal atom bonded to the first linking atom.

14. A display device comprising:
a selection device layer on a substrate;
an optical device layer on the selection device layer; and
an inorganic layer structure disposed on the optical device layer or disposed between the substrate and the selection device layer, the inorganic layer structure comprising: a metal oxide; and an organic linking material including a linking atom bonded to a metal atom of the metal oxide,
wherein the organic linking material includes a first linking atom and a second linking atom, and
wherein at least one of the first linking atom or the second linking atom includes a chalcogen atom.

15. The display device of claim 14, wherein the organic linking material includes a first organic linker and a second organic linker which are adjacent to each other, and
wherein a linking atom of the first organic linker is bonded to a linking atom of the second organic linker.

16. A method of fabricating an inorganic layer structure, the method comprising:
preparing a substrate;
providing a first source including a metal and a second source including oxygen onto the substrate to form a first metal oxide;
providing the first source and a third source including an organic linker having first and second linking atoms onto the first metal oxide to form an organic linking material having the first linking atom bonded to a metal atom of the first source provided on the first metal oxide; and
providing the first source and the second source onto the organic linking material to form a second metal oxide having a metal atom bonded to the second linking atom of the organic linker,
wherein the organic linking material includes a first linking atom and a second linking atom, and
wherein at least one of the first linking atom or the second linking atom includes a chalcogen atom.

17. The method of claim 16, wherein the providing of the first source and the second source onto the substrate to form the first metal oxide is repeatedly performed a plurality of times, and
wherein the providing of the first source and the second source onto the organic linking material to form the second metal oxide is repeatedly performed a plurality of times.

18. The method of claim 17, wherein the number of times to repeat the providing of the first source and the second source onto the substrate to form the first metal oxide is equal to the number of times to repeat the providing of the first source and the second source onto the organic linking material to form the second metal oxide.

19. The method of claim 16, wherein the number of times to repeat the providing of the first source and the third source to form the organic linking material is less than the number of times to repeat the providing of the first source and the second source to form the first metal oxide and the number of times to repeat the providing of the first source and the second source to form the second metal oxide.

\* \* \* \* \*